United States Patent [19]

Tromberg et al.

[11] Patent Number: 5,424,843
[45] Date of Patent: Jun. 13, 1995

[54] APPARATUS AND METHOD FOR QUALITATIVE AND QUANTITATIVE MEASUREMENTS OF OPTICAL PROPERTIES OF TURBID MEDIA USING FREQUENCY-DOMAIN PHOTON MIGRATION

[75] Inventors: Bruce J. Tromberg, Irvine; Tsong T. Tsay, Orange; Michael W. Berns, Trabuco Canyon, all of Calif.; Lars O. Svaasand, Rudolf Raedersu, Norway; Richard C. Haskell, Claremont, Calif.

[73] Assignee: The Regents of the University of California, Oakland, Calif.

[21] Appl. No.: 996,321

[22] Filed: Dec. 23, 1992

[51] Int. Cl.[6] ............... G01N 21/49; G01N 21/59
[52] U.S. Cl. .................................. 356/442; 356/342
[58] Field of Search ............... 356/440, 441, 442, 342, 356/343

[56] References Cited

U.S. PATENT DOCUMENTS 4,929,847  5/1990  Yamazoe et al. ................. 356/442

Primary Examiner—Vincent P. McGraw
Attorney, Agent, or Firm—Daniel L. Dawes

[57] ABSTRACT

Optical measurements of turbid media, that is media characterized by multiple light scattering, is provided through an apparatus and method for exposing a sample to a modulated laser beam. The light beam is modulated at a fundamental frequency and at a plurality of integer harmonics thereof. Modulated light is returned from the sample and preferentially detected at cross frequencies at frequencies slightly higher than the fundamental frequency and at integer harmonics of the same. The received radiance at the beat or cross frequencies is compared against a reference signal to provide a measure of the phase lag of the radiance and modulation ratio relative to a reference beam. The phase and modulation amplitude are then provided as a frequency spectrum by an array processor to which a computer applies a complete curve fit in the case of highly scattering samples or a linear curve fit below a predetermined frequency in the case of highly absorptive samples. The curve fit in any case is determined by the absorption and scattering coefficients together with a concentration of the active substance in the sample. Therefore, the curve fitting to the frequency spectrum can be used both for qualitative and quantitative analysis of substances in the sample even though the sample is highly turbid.

20 Claims, 8 Drawing Sheets

APPARATUS AND METHOD FOR QUALITATIVE AND QUANTITATIVE MEASUREMENTS OF OPTICAL PROPERTIES OF TURBID MEDIA USING FREQUENCY-DOMAIN PHOTON MIGRATION

The Government has rights in this invention pursuant to Contract No. DE-FG03-86ER61227 awarded by the U.S. Department of Energy and Contract No. N00014-91-C0134 awarded by the Office of Naval Research.

BACKGROUND OF THE INVENTION

1. Field of the Invention

The invention relates to the field of optical measurements of turbid media and in particular, relates to an apparatus and method for the measurement of the optical properties of turbid media using frequency-domain photon migration.

2. Description of the Prior Art

The use of short light pulse propagation in multiple scattering media, such as generally described in A. Ishimaru, "*Diffusion of a Pulse in Densely Distributed Scatters,*" J. Opt. Soc. Am. 68, 1045–50 (1978); and K. Shimizu et al., "*Back Scattering of a Picosecond Pulse from Densely Distributed Scatters,*" Appl. Opt. 18, 3484–88 (1979) has found recent application in time domain, tissue optical spectroscopy, B. Chance et al., "*Comparison of Time Resolved and Unresolved Measurements of Deoxy Hemoglobin in Brain,*" Proc. Nat. Acad. Sci. 85, 4971–75 (1988); and D. T. Delpy et. al., "*Estimation of Optical Path Link Through Tissue from Direct Time of Flight Measurement,*" Phys. Med. Biol. 33, 1433–42 (1988). In contrast to previously known continuous illumination techniques such as described by R. F. Bonner et al., "*Model for Photon Migration in Turbid Biological Media,*" J. Opt. Soc. Am. A4 423–32 (1987); and R. A. J. Groenhuis et al., "*Scattering and absorption of turbid materials determined by reflection measurements. 1: Theory,*" Appl. Opt. 22, 2456–62 (1983), pulse propagation methods can provide information about the distribution of scatterers and absorbers in a single measurement. See M. S. Patterson et al., "*Time-resolved reflectance and transmittance for the non-invasive measurement of tissue optical properties,*" Appl. Opt. 28, 2331–36 (1989). These optical properties may be used in a variety of therapeutic and diagnostic techniques, including imaging tissue structure, K. R. Singer et al., "*Image reconstruction of the interior of bodies that diffuse radiation,*" Science 248, 990–93 (1990); R. L. Barbour et al., "*Imaging of subsurface regions of random media by remote sensing,*" Proc. SPIE 1431, Los Angeles, 192–203 (1991); and D. Benaron et al., "*Two-dimensional and 3-D images of thick tissue using time-contrained time-of-flight spectrophotometry,*" Proc. SPIE, Los Angeles, 1641 (in press), in monitoring physiology, E. M. Sevick et al., "*Quantification of time and frequency-resolved optical spectra for the determination of tissue oxygenation,*" Anal. Biochem. 195, 330–51 (*1991*); B. Chance et al., "*Time-resolved spectroscopy of hemoglobin and myoglobin in resting and ischemic muscle,*" Anal. Biochem. 174, 698 (1988); U.S. Pat. No. 4,972,331; and J. M. Schmitt et al., "*Measurement of blood hematocrit by dual-wavelength near IR photoplethysmography,*" Proc. SPIE, 1641, Los Angeles (1992) and in predicting optical symmetry for laser based procedures, S. L. Jacques, et al., "*Modeling Optical and Thermal Distributions in Tissue During Laser Irradiation,*" Lasers in Surgery and Medicine 6, 494–503 (1987).

The conceptional basis for using a time domain approach generally involves solutions to the radiative transfer equation described by K. Furutsu, "*Diffusion equation derived from space-time transport equation,*" J. Opt. Soc. Am. 70, 360 (1980); and M. S. Patterson et al., "*The Propagation of Optical Radiation in Tissue I. Models of Radiation Transport and their Application,*" Lasers in Medical Science 6, 155–68 (1991) using a Monte Carlo simulation, S. L. Jacques, "*Time Resolved Propagation of Ultrashort Laser Pulses within Turbid Tissues,*" Appl. Opt. 28, 2223–29 (1989); and S. T. Flock et al., "*Monte Carlo modeling of light propagation in scattering tissues-I. Model prediction and comparison with diffusion theory,*" IEEE Trans. Biotaed. Eng. 36, 1162–68 (1989) and diffusion theory approximations, K. Shimizu, supra, and A. Ishimaru, "*Diffusion of Light in Turbid Materials,*" Appl. Opt. 28, 2210–15 (1989). Diffusion-base models provide a relatively straight forward analytical expression which describes the shape of a diffusely reflected or transmitted pulse of light in term of the optical properties of the turbid medium. See M. S. Patterson, supra, Appl. Opt. 28. Thus, the observed behavior of an ultra short light pulse can be mathematically related to the large number of optical paths available in multiple scattering media. Since introduction of losses or absorbers reduces the average path length between scattering events, the absorber-dependent changes in pulse propagation time can be used to calculate the absorption coefficients of the light in the turbid media. See Patterson, supra, Appl. Opt. 28.

Frequency domain methods can also similarly be adapted to diffusion theory models. It has been suggested in the prior art that amplitude modulated light propagates through homogeneous, multiple scattering media as diffuse waves with a coherent front. See J. Fishkin et al., "*Diffusion of intensity modulated near infrared light in turbid media,*" Proc. SPIE, 1431, Los Angeles (1991). These photon density waves are characterized by a phase velocity, $V_p$, and a modulation wavelength, $\lambda_m$, that are primarily functions of the optical properties of the media. Diffuse wave properties, of course, bear no relationship to corresponding electromagnetic wave features, since in a turbid media, the phase relationships between optical waves vary in a rapid stochastic manner.

The analytical power and simplicity of frequency domain methods have been demonstrated in tissue studies up to 3 GHz, J. P. Lakowicz et al., "*Frequency domain measurements of photon migration in tissue,*" Chemical Physics Letters 166, 246–52 (1990) and measurements of hemoglobin saturation at a single modulation frequency have also been reported, E. M. Sevick, supra. Analytic expressions have been derived for frequency domain analysis of the scattering of light in semi-infinite media from a Fourier transform of a time domain relation. See M. S. Patterson et al., "*Frequency-domain reflectance for the determination scattering absorption properties of tissue,*" Appl. Opt. 30, 4474–76 (1991). In general, frequency-domain measurement techniques are real time recordings which, in comparison to the alternative time-domain methods, place much less stringent demands on the bandwidth of the light source and detector. Thus, the instrumentation cost can be relatively modest when laser diodes and photomultiplier tubes are employed.

What is needed is an application of the advantageous features of frequency domain methods to make practical frequency domain measurements of turbid media.

BRIEF SUMMARY OF THE INVENTION

The invention is an optical method of analysis of turbid media. The invention comprises the steps of generating a modulated light beam. A sample of the turbid media is exposed to the modulated light beam. The radiance of the modulated light beam returned from the sample is measured. Optical or chemical properties of the sample are determined from the measured returned radiance. As a result, the sample may be analyzed whether the sample is highly scattering, highly absorptive or a combination of both.

The step of generating the modulated light beam comprises generation of the modulated light beam at a plurality of frequencies. The step of generating the plurality of frequencies comprises the step of modulating the light beam at a fundamental frequency and a plurality of integer harmonics thereof. In the illustrated embodiment the fundamental frequency is 5 megahertz and wherein the integer harmonics are generated therefrom to modulate the light beam at 5, 10, 15 MHz and the like. Other fundamental frequencies and harmonics could be employed without departing from the spirit and scope of the invention. In addition the plurality of frequencies need not have a harmonic relationship to each other. Any method of generating multiple frequencies can be substituted. For example, a plurality of frequencies from a ramped frequency synthesizer can also be equivalently employed. The essential concept is to generate information at multiple modulation frequencies in order to fully characterize the frequency response of the sample.

The step of measuring the radiance is performed at each of the plurality of modulated frequencies and the step of determining comprises the step of providing a complete curve fit in the frequency domain in a computer automated process for at least one optical parameter derived from the radiance at the plurality of modulated frequencies, such as phase lag or modulation relative to a reference beam. The curve fit is determined by the coefficient of absorption and the coefficient of scattering for the sample so that the sample can be quantitatively analyzed by identification of its optical absorption and scattering coefficients. The method further comprises the step wherein the results of the curve fit are used to calculate the molar concentration of an absorbing substance within the sample.

The invention is also not restricted to a single wavelength or color for making measurements as described in the illustrated embodiment below. The optical wavelength can be varied and the phase and modulation determined as a function of optical wavelength or optical frequency, as opposed to the modulation frequency. This provides a qualitative description of the spectral properties of the medium. When the phase and modulation data are fit to their respective equations or curves as described below, the absorption spectrum and wavelength-dependent scattering properties can be recovered. These properties then allow the medium to be qualitatively identified.

If the sample is highly absorptive, the step of determining comprises the step of providing a linear curve fit in the frequency domain to at least one optical parameter derived from the measured radiance, such as phase lag or modulation relative to a reference beam, at and below a predetermined frequency. The linear curve fit is determined by the absorption coefficient of the sample so that qualitative determination of the sample may be made. The method further comprises the step of determining the linear curve fit below the predetermined frequency according to concentration of a substance included within the sample so that quantitative determination of the substance may be made.

The step of measuring the radiance comprises the derivation of modulation of the light. The modulation is defined as modulation of light returned from the sample relative to modulation of the light exposed on the sample. The step of measuring the radiance also comprises the derivation of the phase lag of the light. The phase lag is defined as the phase of light returned from the sample relative to the phase of the light exposed on the sample.

The step of measuring the radiance comprises the steps of receiving the returned light beam from the sample in a sensing device having a gain. The gain of the sensing device is modulated at a fundamental frequency increased by a cross correlation frequency and integer multiharmonics thereof. The step of determining comprises the step of analyzing phase and modulation amplitude response at each of the harmonic cross frequencies returned from the sample. The step of analyzing comprises transforming phase and modulation response return from the sample to a frequency spectrum.

The invention is also characterized as an apparatus for analyzing turbid media comprising a source of light for exposing a sample to a modulated beam of light. An optical detector receives at least a portion of the modulated beam of light returned from the sample. A circuit analyzes the returned modulated light beam from the sample at a cross frequency of the frequency of modulation of the beam of light. Another circuit or array processor provides a frequency spectrum of the analyzed light at the cross frequency. A computer provides a curve fit to the frequency spectrum according to modulation frequency, optical absorption coefficient, and optical scattering coefficient as curve fitting parameters. As a result, characteristics of the sample are identified whether the sample is high absorptive, highly scattering or both.

The source for exposing the sample to the modulated beam of light modulates the light beam at a predetermined fundamental frequency and integer harmonics thereof.

The circuit for analyzing the returned light beam from the sample at the cross frequency preferentially detects the return light beam at a plurality of integer harmonics above the fundamental frequency.

The computer for providing a curve fit to the frequency spectrum provides a complete nonlinear curve fit at the plurality of cross frequency harmonics so that a highly scattering sample may be analyzed. In the alternative the computer provides a linear curve fit to the frequency spectrum at and below a predetermined frequency so that a highly absorptive sample may be analyzed.

The invention may be better visualized by viewing the embodiments in the following drawings wherein like elements are referenced by like numerals.

BRIEF DESCRIPTION OF THE DRAWINGS

FIGS. 8a and 8b are graphs which illustrate the utility of a linear fit determination of the optical scattering and absorption coefficients in a highly absorptive material.

Figure 1:
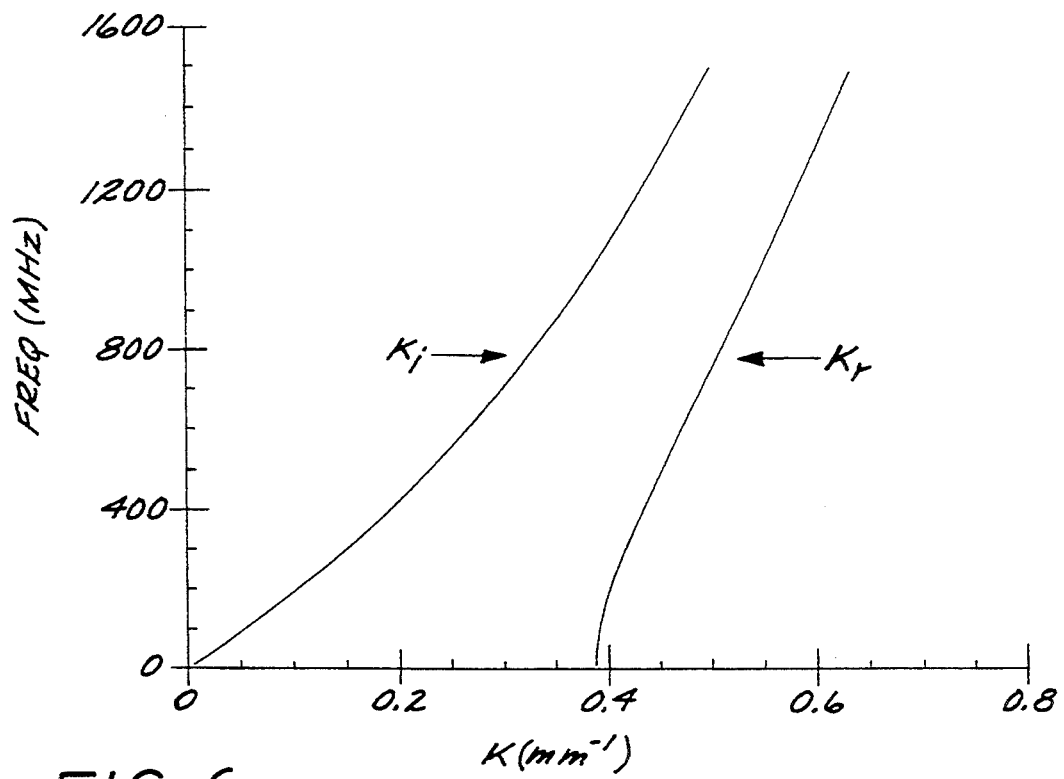
FIG. 1 is a graphic depiction of the values of the real and imaginary components of the wave number as a function of frequency for a sample with tissuelike optical properties.

The invention now having been illustrated in the drawings discussed above, consider the various embodiments of the invention as described in the following detailed description.

DETAILED DESCRIPTION OF THE PREFERRED EMBODIMENTS

Optical measurements of turbid media, that is media characterized by multiple light scattering is provided through an apparatus and method for exposing a sample to a modulated laser beam. The light beam is modulated at a fundamental frequency and at a plurality of integer harmonics thereof. Modulated light is returned from the sample and preferentially detected at cross frequencies at frequencies slightly higher than the fundamental frequency and at integer harmonics of the same. The received radiance at the beat or cross frequencies is compared against a reference signal to provide a measure of the phase lag of the radiance and modulation ratio relative to a reference beam. The phase and modulation amplitude are then provided as a frequency spectrum by an array processor to which a computer applies a complete curve fit in the case of highly scattering samples or a linear curve fit below a predetermined frequency in the case of highly absorptive samples. The curve fit in any case is determined by the absorption and scattering coefficients of the sample. Therefore, the curve fitting to the frequency spectrum can be used both for qualitative and quantitative analysis of substances in the sample even though the sample is highly turbid.

Before considering the apparatus and methodology of the invention, it will be necessary to have an brief understanding of the optical theories upon which the invention is based. Consider then an analytical solution of the time dependent diffusion equation assuming an infinite media for sinusoidally amplitude-modulated light waves. The object is to derive a quantitative general model of the unique characteristics of photon density waves in turbid media.

Optical behavior in multiple scattering media, such as tissue, paint, milk, or any other type of media in which multiple scattering events of the light occur, is typically characterized by the quantities, $\phi$, which is the radiant energy fluence rate and L, the radiance. The radiant energy fluence rate, $\phi$, is defined as the optical energy flux incidence on infinitesimally small sphere divided by the cross sectional area of the sphere. See equation 1.

$$\phi = \int_{\Omega = 0}^{4\pi} L \, d\Omega \tag{1}$$

Since the integration is taken over the entire solid angle, the fluence rate is a measure of the total optical flux at a point. The radiance, L, is the optical energy flux in a direction per unit of solid angle per unit area orthogonal to the direction. In a completely isotropic light field, the radiance is described by equation 2.

$$L = \phi/4\pi \tag{2}$$

When the optical flux is viewed along the axis of a solid angle element, $d\Omega$, the irradiance, E, gives the flux per unit area orthogonal to the axis of view and can be expressed as equation 3.

$$E = \int_{\Omega = 0}^{2\pi} L \, (-\vec{l} * \vec{n}) d\Omega = \pi L = \phi/4 \tag{3}$$

Where the vectors 1 and n are respectively the unit vectors along the axis of view and the outward unit surface normal to the solid angle element.

As diffuse protons propagate through a turbid media, such as tissue, the irradiance, E, onto the element of a surface, such as a photodetector, will vary with respect to the source location. When the surface normal points towards the source, the irradiance, E is enhanced and is described by equation 4

$$E = \phi/4 + j/2 \tag{4}$$

where j is the magnitude of the transport vector j representing the total deviation from a completely isotropic distribution. Similarly, the irradiance, E, is reduced from the surface normal points directly away from the source of irradiation and thus is described by equation 5.

$$E = \phi/4 - j/2 \tag{5}$$

This deviation is a consequence of the diffusion process since the net transport of diffuse photons in any directions must be expressed by a higher radiance in the direction of transport.

It can be shown that the radiance contributed by the net transport of diffuse photons is given by a term of $(3j * 1/4)$. According to Fick's Law:

$$\vec{J} = -\theta \Delta \phi \tag{6}$$

where $\theta$ is a photon diffusion constant which in turn is a function of the scattering coefficient $\sigma$ and absorption coefficient $\beta$ given by equation 7.

$$\rho = \frac{1}{3(\sigma(1-\delta) + \beta)} = \frac{1}{3(\sigma_{\mathit{eff}} + \beta)} \quad (7)$$

Where the effective scattering coefficient, $\theta \mathit{eff}$, is determined by the average cosine of the scattering angle, g. J from equation 6 can be substituted into the diffusion wave equation as a function of the radiant energy fluence rate, $\phi$, to derive a spatial and temporal solution to the wave occasion given by equation 8.

$$\rho(\vec{r},t) = \frac{\phi_o e^{-r/\delta}}{r} + \frac{\phi_r e^{k_r r}}{r} e^{i(k_i \vec{r} - t)} \quad (8)$$

In equation 8, the first term in the sum is the time independent or DC component, while the second term in the sum is the time dependent or AC component of a spatially and temporally varying source rate, $\phi(r,t)$; $\omega$ is the angular modulation frequency; and $k_r$ and $k_i$ are the real or imaginary components of the complex wave number k. The DC penetration depth is given by $\delta$ which is expressed below in equation 9.

$$\delta = \frac{1}{\sqrt{3\beta(\beta + \sigma_{\mathit{eff}})}} = \sqrt{X\tau} \quad (9)$$

Where $\tau$ is the optical absorption relaxation time, $X = \theta c$, and c is the velocity of light in the medium. The photon density wave in the diffuse media has a phase velocity $V_p$ given by equation 10 and a modulation wavelength $\lambda_m$ given by equation 11, both which are functions of the imaginary component of the wave number.

$$V_p = \omega/k_i \quad (10)$$

$$\lambda_m = 2\pi/k_i \quad (11)$$

The modulation wavelength and photon density wave phase velocity describe collective properties of the diffusion density waves and do not describe the behavior of individual photons. In particular $\lambda_m$ and $V_p$ are respectively measures of the minimum distance and space between regions with the same phase of diffuse photon density and phase from propagation velocity.

It is known that a photon density wave flowing in infinite medium has real or imaginary components of the complex wave number given by equation 12.

$$k_r = \frac{1}{\sqrt{2X\tau}} \sqrt{\sqrt{1 + (\omega\tau)^2} + 1} \quad (12)$$

$$k_i = \frac{1}{\sqrt{2X\tau}} \sqrt{\sqrt{1 + (\omega\tau)^2} - 1}$$

The values of the real and imaginary components of the wave number are a function of frequency and are graphically depicted in FIG. 1 for a sample with tissue-like optical properties, namely X equals $1.5 \times 10^4$ meters squared per second and $\tau$ equals 0.44 nanoseconds. It turns out, however, that the general shape of the frequency dependence of the k functions in FIG. 1 is substantially independent of the optical properties of the material. Changes in X and $\tau$ simply change the domain or limits of the high or low frequency domains. For example, in a high frequency domain where $\omega$ is very much greater than $1/\tau$ and the real or imaginary parts of the wave number are approximately equal, both equaling $$k_r \approx k_i \approx \sqrt{\frac{\omega}{2X}},$$

the density wave properties are dominated by scattering. The wave density is heavily damped with a constant attenuation of $e^{-2\pi r/\lambda_m}$. Therefore the amplitude is reduced by approximate 0.19 percent of its initial value after traveling a distance of $\lambda_m$ and the phase velocity is given by $V_p = \omega/k_i = \sqrt{2X\omega}$.

As the modulation frequency is reduced, light is collected from larger regions and the phase velocity increases. This trend continues until the phase velocity is independent of the modulation frequency, typically where $\omega$ is substantially less than $1/\tau$ and then the wave properties are dominated by absorption as discussed below.

At higher frequencies, however, there is greater attenuation and the light is collected from smaller regions. The time required to achieve a steady state photon distribution is reduced and the phase velocity increases with the $\sqrt{\omega}$. Multiple scattering cannot occur, however, when the modulation frequency is greater than the reciprocal of the average time between scattering events, that is when $\omega$ is substantially less than $c\sigma_{\mathit{eff}} = 1/\tau_{sc}$. Diffusion theory is generally only valid when the dominant mechanism involves multiple scattering. Therefore, the upper frequency limit to diffusion theories is imposed by the scattering relaxation time, $t_{sc}$. In living tissues with the effective scattering coefficient on the order of 50 cm$^{-1}$ this corresponds to an upper frequency limit with respect to the validity of diffusion theory of approximately 180 GHz.

In the low frequency regime, however, where $\omega$ is substantially less than $1/\tau$, the phase velocity reaches a dispersionless lower limit which is dependent upon the modulation frequency. In this case, the solutions for the complex and real components of the wave number reduce to the form shown in equation 13.

$$k_i \approx \frac{\omega\tau}{2\sqrt{X\tau}} \quad (13)$$

$$k_r \approx \frac{1}{\sqrt{X\tau}} = \frac{1}{\delta}$$

With the phase velocity $$V_p = 2\sqrt{\frac{X}{\tau}}.$$

In the graphic depiction of FIG. 1, the lower frequency behavior occurs at modulation frequencies well below $\omega = \beta c$, i.e. in the illustrated embodiment of FIG. 1 at or below 360 MHz. When $\omega$ is particularly small relative to $1/\tau$, the AC and DC attenuation rates are approximately equal. FIG. 1 clearly illustrates this frequency independent region when $k_r$ approaches the reciprocal of the DC penetration depth δ as described above in the approximation equation 13. As ω increases, however, some frequency dependence is observed. Provided that ωτ is less than 0.7, $k_r$ can be expanded in powers of ωτ and it can be shown that dispersionless attenuation ranges from a frequency independent limit where $k_r$ is approximately equal to 1/δ to an upper boundary where $k_r$ is proportional to $1+^{(\omega\tau2/\delta)}$.

Frequency domain measurements are used to record the phase of the light, φ, and the modulation amplitude, m, with respect to a source response. Since these parameters can be defined in terms of a complex wave number, k and m are simply functions of β, r and the optical properties of the material, τ and σeff. These functional relationships are described below in equation 14.

$$\phi = k_i r = r\sqrt{\beta(\beta + (1-\delta)\sigma)} \sqrt{\frac{3}{2}} \sqrt{\sqrt{1 + \left(\frac{\omega}{\beta c}\right)^2} - 1} \quad (14)$$

$$-\ln(m) = -\ln[(AC/DC)_{sample}/(AC/DC)_{source}]$$

$$= r\sqrt{\beta(\beta + (1-\delta)\sigma)} \sqrt{\frac{3}{2}} \left[\sqrt{\sqrt{1 + \left(\frac{\omega}{\beta c}\right)^2} + 1} - \sqrt{2}\right]$$

The phase and the modulation amplitude can be computed from measurements of the phase and magnitude or the radiance, L, and then, given the modulation frequency, ω, the scattering coefficient and absorption coefficient determined from equation 14.

Figure 2:
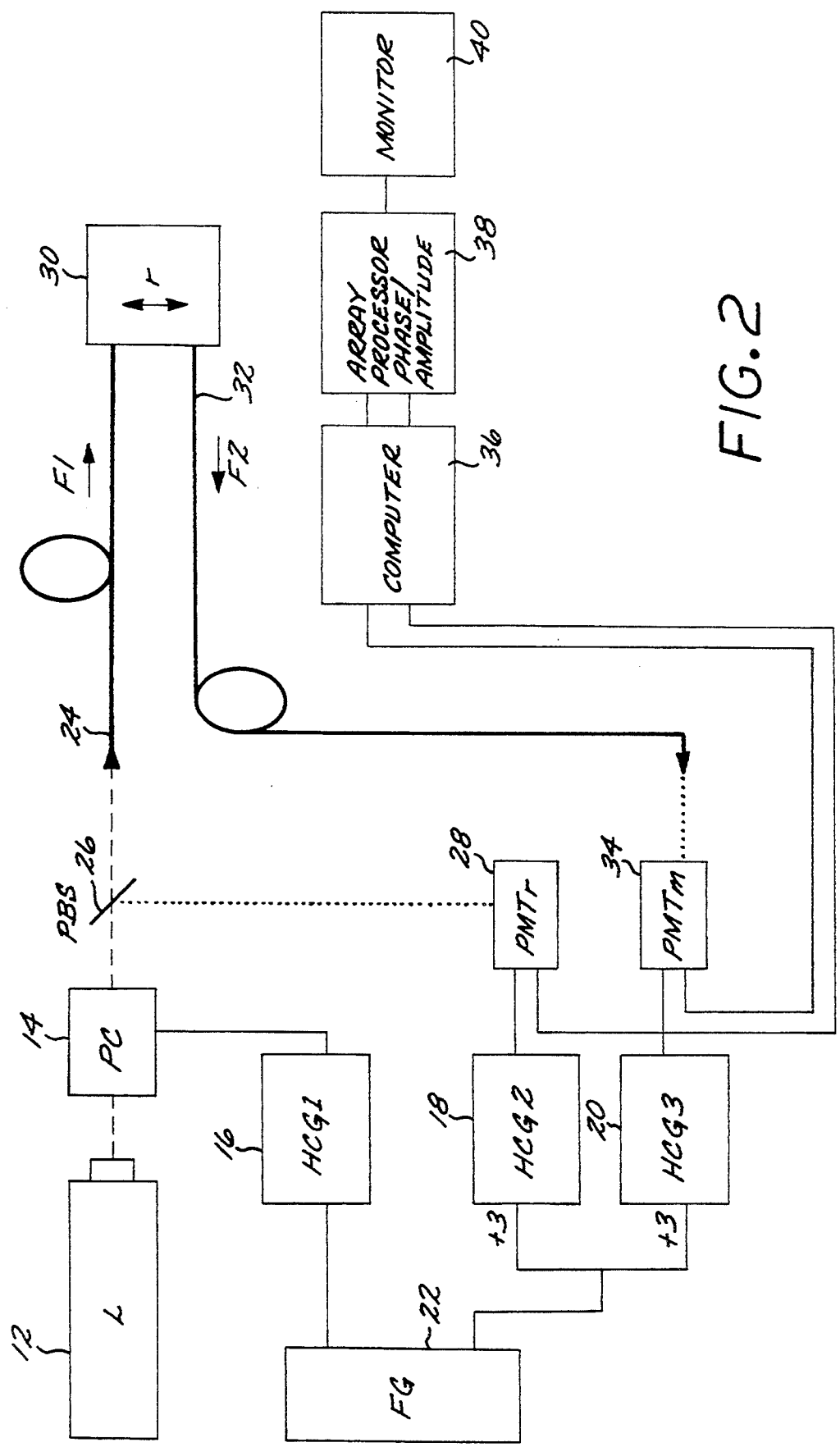
FIG. 2 is a simplified block diagram of an instrument for performing the methodology of the invention.

The theory behind the measurement now having been described turn to the instrumentation system of FIG. 2 wherein the methodology of the invention is illustrated. The instrument can be described as a photon migration instrument including a modified multiharmonic Fourier transform phase and modulation fluorometer, model 48000 MHF manufactured by SLM of Champaign, Ill. A light source 12 is provided in the form of either a water cooled argon ion laser such as an Innova 90-5 built by Coherent of Palo Alto, Cal., or an argon pumped dye laser sold as a coherent model 599 with DCM dye. In the illustrated embodiment a single wavelength, 514 nm, is modulated. However, as briefly discussed above this optical wavelength can be varied to develop sets of data or absorption spectra.. In addition, the specific choice of optical wavelength, even when fixed, is largely arbitrary and is chosen in a manner consistent with the teachings of the invention according to conventional design choices.

Light emitted from laser 12 is switched by a Pockel cell 14. Pockel cell 14 is driven either by a frequency synthesizer or indirectly as in the case of FIG. 2 by the amplified output of a harmonic comb generator 16 which is used to modulate the light at single frequencies or to produce pulses with high harmonic content in a multiharmonic mode.

When the system of FIG. 2 is operating in a multiharmonic mode, phase and modulation data for more than 60 different frequencies up to 250 MHz can be acquired in a few seconds. In the illustrated embodiment, three harmonic comb generators 16, 18 and 20 have their inputs coupled to a frequency source 22 which is operating at 5 MHz and at 5 MHz plus 3 Hz (5,000,003 Hz). The outputs of comb generators 16–20 are, in the time domain, 2 nsec. pulses spaced at 200 nsec intervals. In the frequency domain these outputs can be considered as having a fundamental frequency of 5 MHz with integer harmonics of 5 MHz, 10 MHz, 15 MHz and so on in 5 MHz steps.

The pulse from harmonic comb generator 16 is amplified (by circuitry not shown) and applied as a driving input signal to the Pockel cell 14. Light through Pockel cell 14 is thus modulated to have a high harmonic content and is optically focused on a 600 micron diameter fused silica optic fiber probe 24. A partially silvered mirror 26 diverts a small portion of the modulated light from Pockel cell 14 to a reference photomultiplier tube 28. In the illustrated embodiment a Hamamatsu model R928 photo tube is used. Photomultiplier tube 28 in turn is powered by harmonic comb filter 18 and the output of photomultiplier tube 28 is used for phase and modulation locking in instrument 10.

The bulk of the light from Pockel cell 14 is directed onto optic fiber 24 and is transmitted along the fiber into sample 30. A second optic fiber 32 is used as a sensing probe to collect light scattered from sample 30 and is delivered to photomultiplier tube 34, which is also a Hamamatsu model R928 photomultiplier. In the illustrated embodiment the active ends of fibers 24 and 32 are immersed in the medium to simulate an infinite medium. However, the invention is also practiced as semi-infinite model with the ends of fibers 24 and 32 placed on the surface of the medium. This may alter the exact forms of the equations from those recited here, but the underlying principles are the same. Still further the invention is also practiced with relatively thin samples of the order of a few centimeters in thickness by having the receiving optic fiber positioned on the opposing side of the media from the transmitting optic fiber. Again, this may alter the exact forms of the equations from those recited here. Regardless of the boundary conditions of the medium in which measurements are made, the method of the invention allows quantitative optical spectroscopy measurements to be remotely performed through the optic fibers so that molecular absorbers and scatterers in turbid media can be completely characterized in their natural, undiluted state at the actual process or utilization sites in other systems.

The gain of photomultiplier tubes 28 and 30 is modulated by comb filters 18 and 20 respectively. The output of harmonic comb filters 18 and 20 are the frequencies of 5 MHz plus 3 Hz, 10 MHz plus 6 Hz, 15 MHz plus 9 Hz, and so forth. This off-frequency modulation of the detected signal is used to create a beat frequency at the 3, 6, 9 ... Hz beat frequencies or cross correlation frequencies. The signal related to the detected phase and amplitude of light scattered from sample 30 at the cross correlation frequencies of 3, 6, 9 ... Hz is sampled and digitized by a dual channel analog-to-digital converter 36. The reference signal from photomultiplier 28 is also input to channel analog-to-digital converter 36. Measurements from reference photomultiplier tube 28 and sample photomultiplier tube 34 are interleaved and as described above cross correlation detection is employed. See J. R. Lakowicz, "*Principles of Fluorescent Spectroscopy,*" Plenum Press, New York (1983) at page 78 incorporated herein by reference.

An array processor 38 performs the Fourier frequency transform on the phase and amplitude at the cross correlation frequencies and converts the digital data for the phase and amplitude to a frequency spectrum ranging from 3 Hz to approximately 150 Hz. In the illustrated embodiment array processor 38 is included in the SLM fluorometer identified above.

The phase and modulation information from the higher frequency components of the harmonic comb function ranging from 5 MHz to 250 MHz is contained within the 3 to 150 Hz spectrum. Phase and modulation values are computed from the real and imaginary components of the frequency transform by computer 40, which in the illustrated embodiment is a Mac Intosh personal computer.

Instrument 10 of FIG. 2 can be used to make measurements at a single frequency simply by eliminating the harmonic comb filter 16-20 and tuning frequency synthesizer 22 to the desired frequency, which would be directly coupled to Pockel cell 14 and photomultiplier tubes 28 and 34.

In the illustrated embodiment, sample 30 is contained within a 37 cm by 37 cm black walled cylindrical vessel having a 10 liter capacity. In the illustrated embodiment, 10 liters of an emulsified fat solution, Intralipid, manufactured by Kabi Vitrum, Inc. of Clayton, N.C. was used to fill the container for sample 30. Optical fibers 24 and 32, which have a 600 micron core diameter and flat cut faces, were positioned in the center of liquid parallel to each other. The central position within sample 30 was carefully selected in order to simulate an infinite medium. The distance between source and collection fibers 24 and 32 respectively can be systematically varied, which in the illustrated embodiment contemplated a variation between 5 and 20 millimeters to comprise a series of measurements. A reference measurement was similarly recorded in air with the input fiber 24 and collection fiber 32 facing each other.

A porphyrin compound, tetraphenylporphine tetrasulfinate, TPPS$_4$, manufactured by Porphyrin Products of Logan, Utah, was added to the Intralipid solution in the illustrated embodiment to provide an absorber. The 514 nanometer laser line filter manufactured by Corion Corporation of Hollister, Mass. was placed at the optical window of photomultiplier tube 34 in order to block fluorescence from the porphyrin compound, TPPS$_4$ and to isolate the scattered light.

However, it is entirely within the scope of the invention that fluorescence or more generally luminescences, could be measured and exploited to devise a spectrofluoroscope. When luminescent molecules are in turbid media, the frequency dependent response provides information regarding absorption, scattering, and radiative lifetimes. The wavelength-dependent properties of the luminescence can be evaluated in a similar manner by recording phase and modulation as a function of luminescence wavelength.

Figure 3A:
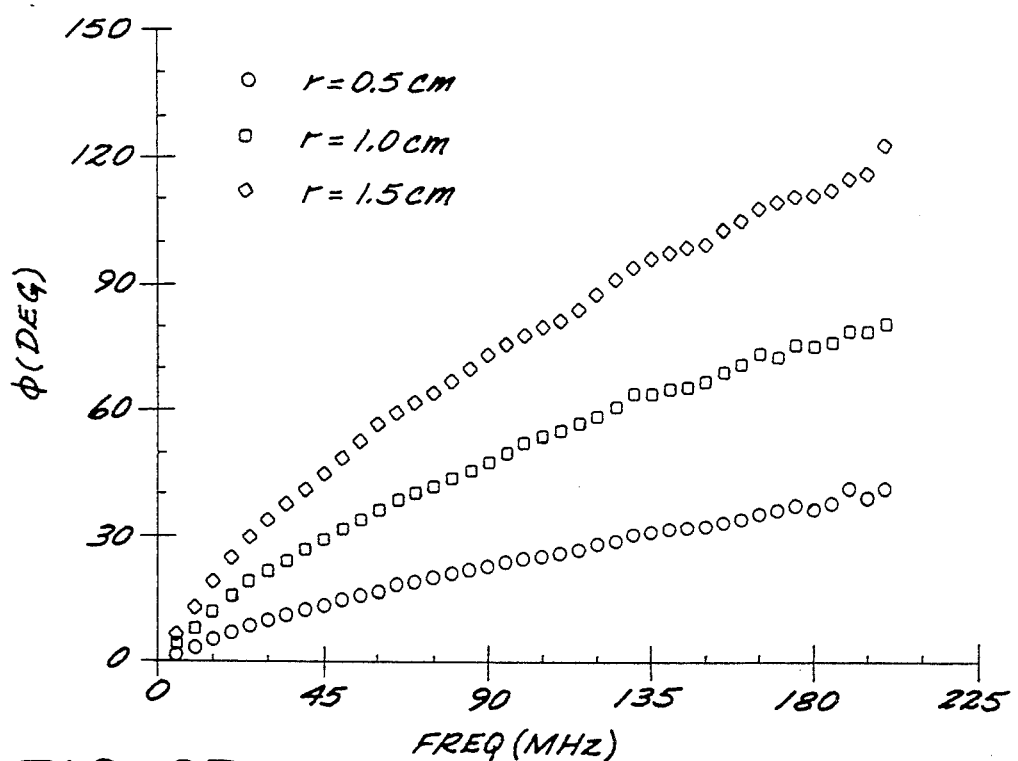
FIGS. 3a and 3b are graphs which illustrates the phase and modulation respectively attained for three measurements across a frequency range with different separation distances between the optical fibers within sample.
Figure 3B:
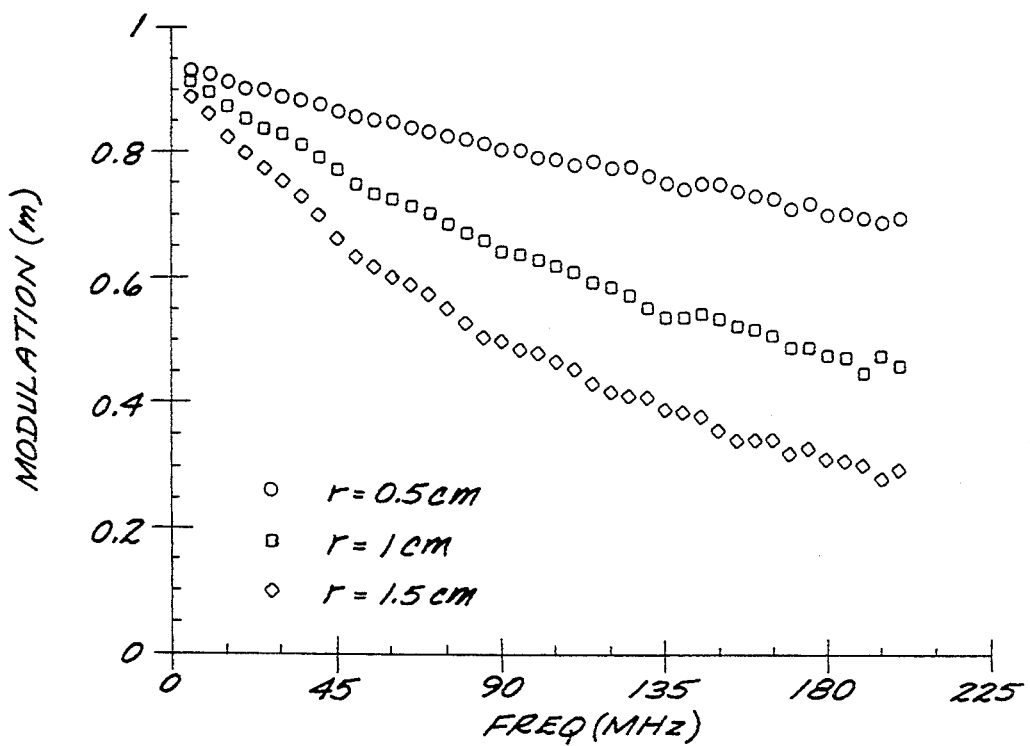

FIGS. 3 and 3$b$ illustrate the phase and modulation respectively attained for three measurements across a frequency range with different separation distances between the optical fibers within sample 30. The data illustrates the performance of instrument 10 in FIG. 2 for various frequencies between 5 and 200 MHz with a 2 percent Intralipid solution. In each case, the frequency response of the phase and modulation is substantially nonlinear no matter what the distance between the optical fibers within sample cell may be. This implies a density wave dispersion over most of the modulation region. It also illustrates that relatively small changes in fiber separation substantially influence the absolute magnitude of the phase and modulation values.

Figure 4A:
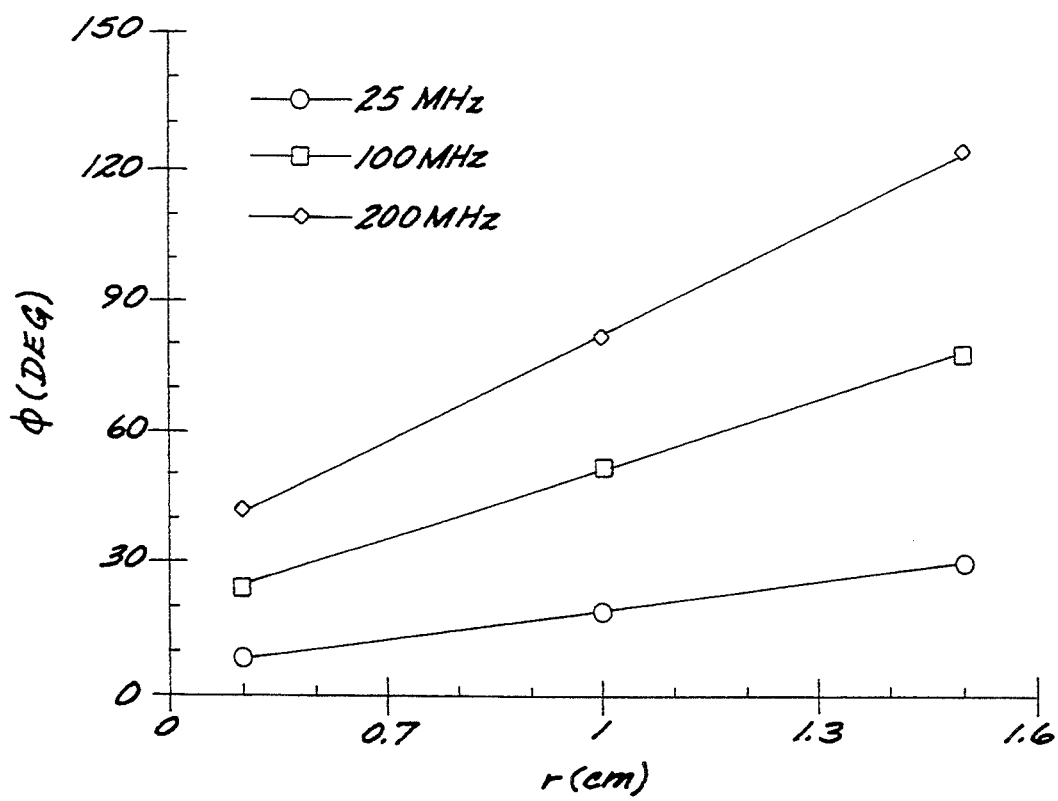
FIGS. 4a and 4b are graphs of phase and modulation respectively as a function of the separation distance between the fibers at different frequencies.
Figure 4B:
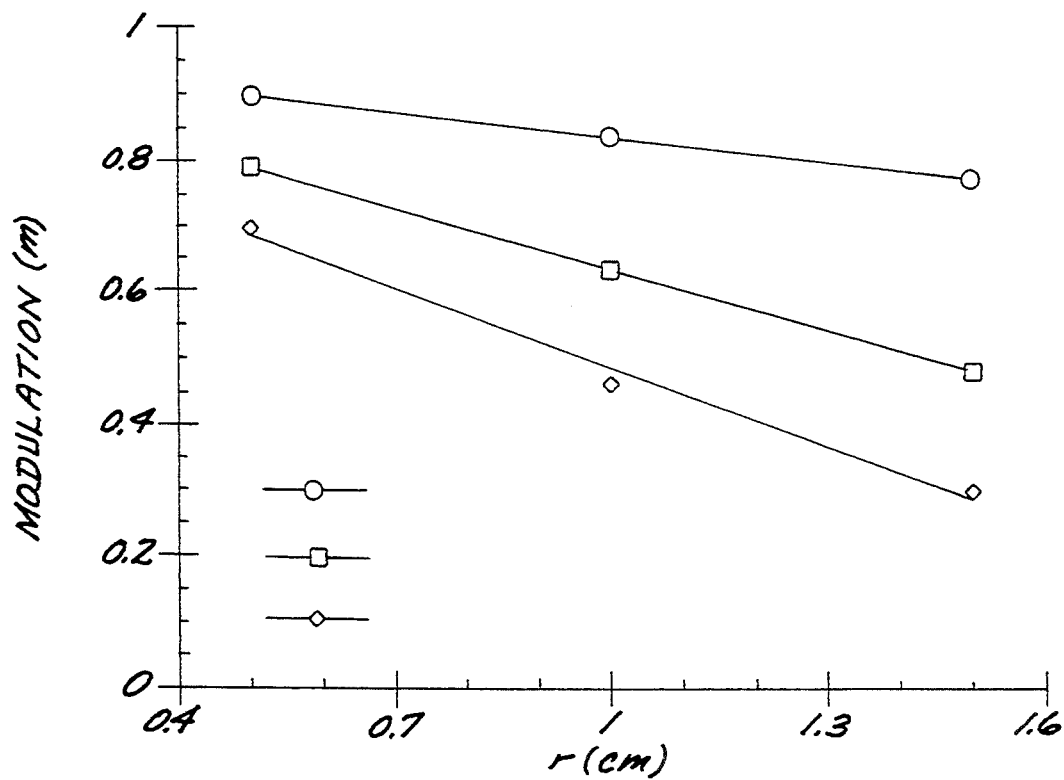

Phase and modulation are graphically depicted in FIGS. 4$a$ and 4$b$ respectively as a function of the separation distance between the fibers at different frequencies. Fiber distance thus has a linear relationship at all frequencies to both phase and modulation. Higher frequencies result in shorter modulation wavelengths or more photon density fluctuations in a given distance. Attenuation and phase lag increase as modulation wavelength is reduced, therefore illustrating an increase in the measured phase and a decrease in the measured modulation values with increasing modulation frequency.

Figure 6:
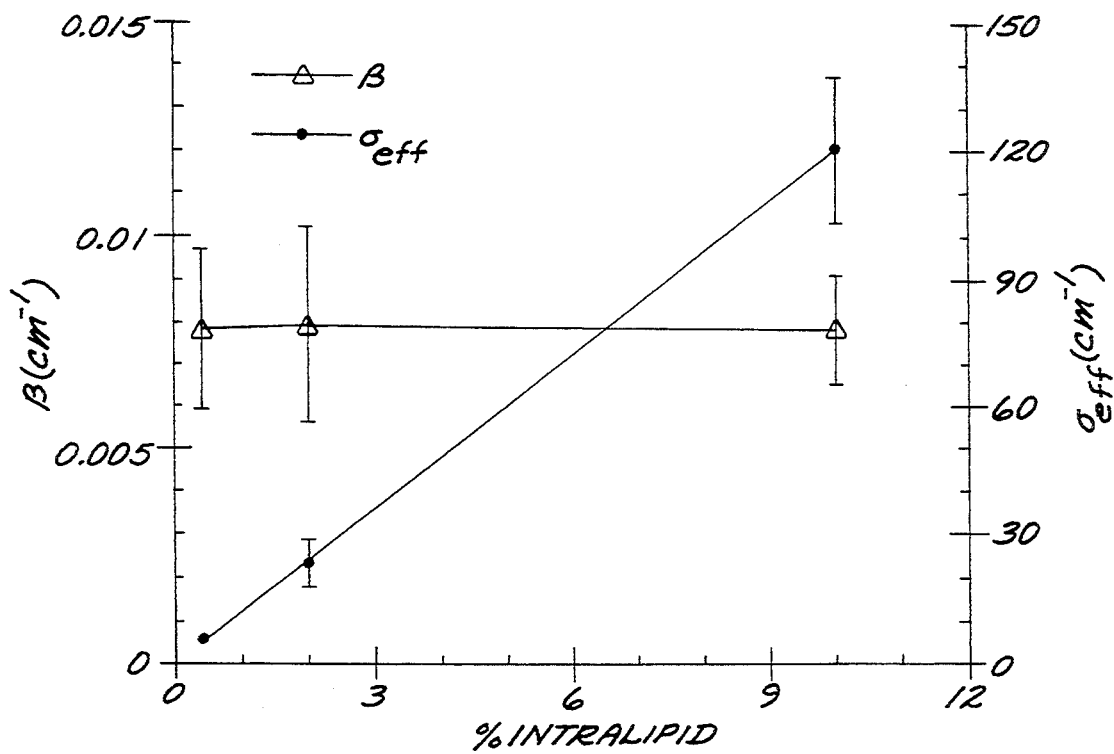
FIG. 6 is a graph of the results of a computation on the data of FIGS. 5a and 5b. Each of the scattering and absorption coefficient values shown in FIG. 6 is an average of the phase and modulation estimates at three different inter-fiber differences.

In the graphic depictions of FIGS. 5$a$ and 5$b$, phase and modulation as a function of frequency is depicted for fibers placed at a fixed separation distance of one centimeter in various concentrations Intralipid samples. The values for the effective scattering coefficient and absorption coefficients can be calculated from the data of FIGS. 5$a$ and 5$b$ using equation 14 provided there is sufficient nonlinearity, that is substantial dispersion behavior, to allow for a reliable least squares fit to the data. The results of such a computation on the data of FIGS. 5$a$ and 5$b$ are illustrated in the graphic depiction of FIG. 6. Each of the scattering and absorption coefficient values shown in FIG. 6 is an average of the phase and modulation estimates at three different inter-fiber differences. FIG. 6 illustrates that the absorption coefficient, $\beta$, is relatively insensitive to changes in the concentration of scattering solution, while commensurate changes in the effective scattering coefficient are obtained with variations in the concentration of scattering fluid.

Alternatively, instead of using the nonlinear least squares full fit curve, depicted in FIGS. 5$a$ and 5$b$, portions of those curves below approximately 20 MHz can be used in a linear approximation of equation 18 which is expressed below in equation 15.

$$\phi = k_i r = \frac{\sqrt{\frac{3}{2} \sigma_{eff}}}{c \sqrt{2\beta}} \omega \tag{15}$$

$$-\ln(m) = k_r - \frac{1}{\sqrt{X_T}} = \frac{\sqrt{\frac{3}{2} \sigma_{eff}}}{c \sqrt{2\beta}} \frac{r\omega^2}{4\beta C}$$

This leads to a functional relationship between $\phi$ and frequency which is linear and to modulation which is a simple quadratic of frequency. These relationships in turn lead to constant slopes $m_{100}$ and $m_{-\ln m}$ which can be used to derive the value of the absorption coefficient, $\beta$, which is independent of r given below in equation 16.

$$\beta = m_{100}/4cm_{-\ln(m)} \tag{16}$$

Figure 5A:
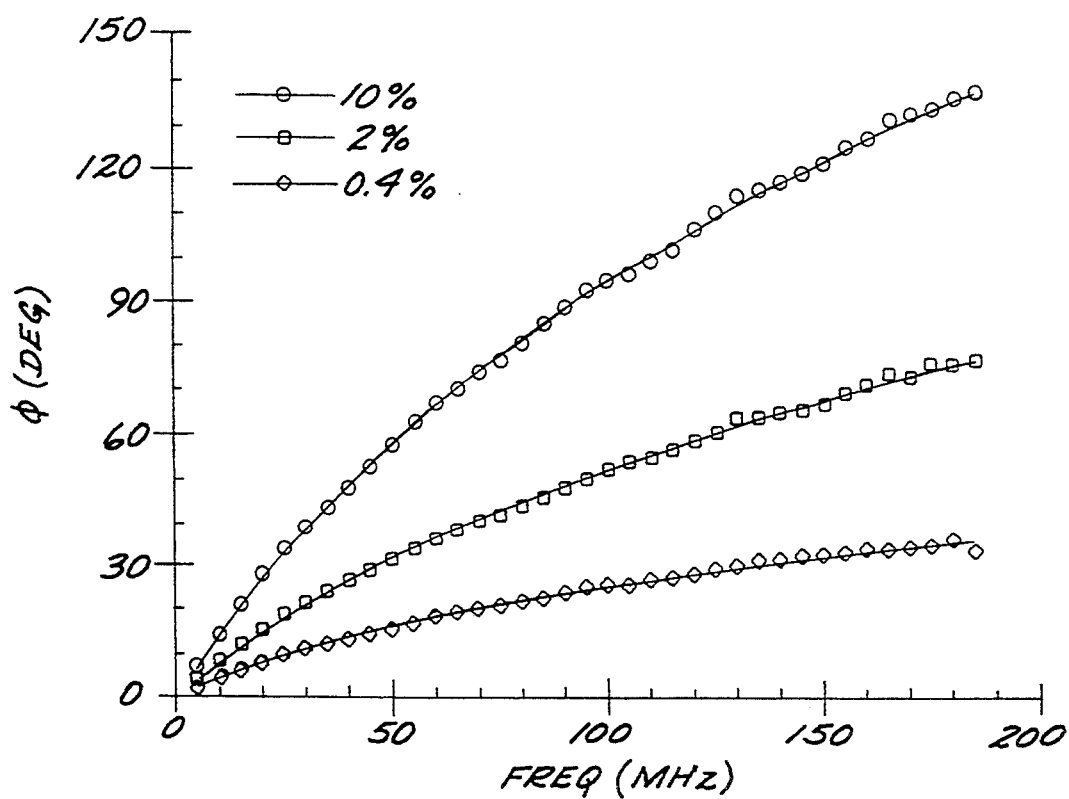
FIGS. 5a and 5b are graphs which illustrate phase and modulation as a function of frequency for fibers placed at a fixed separation distance of one centimeter in various concentrations Intralipid samples.
Figure 5B:
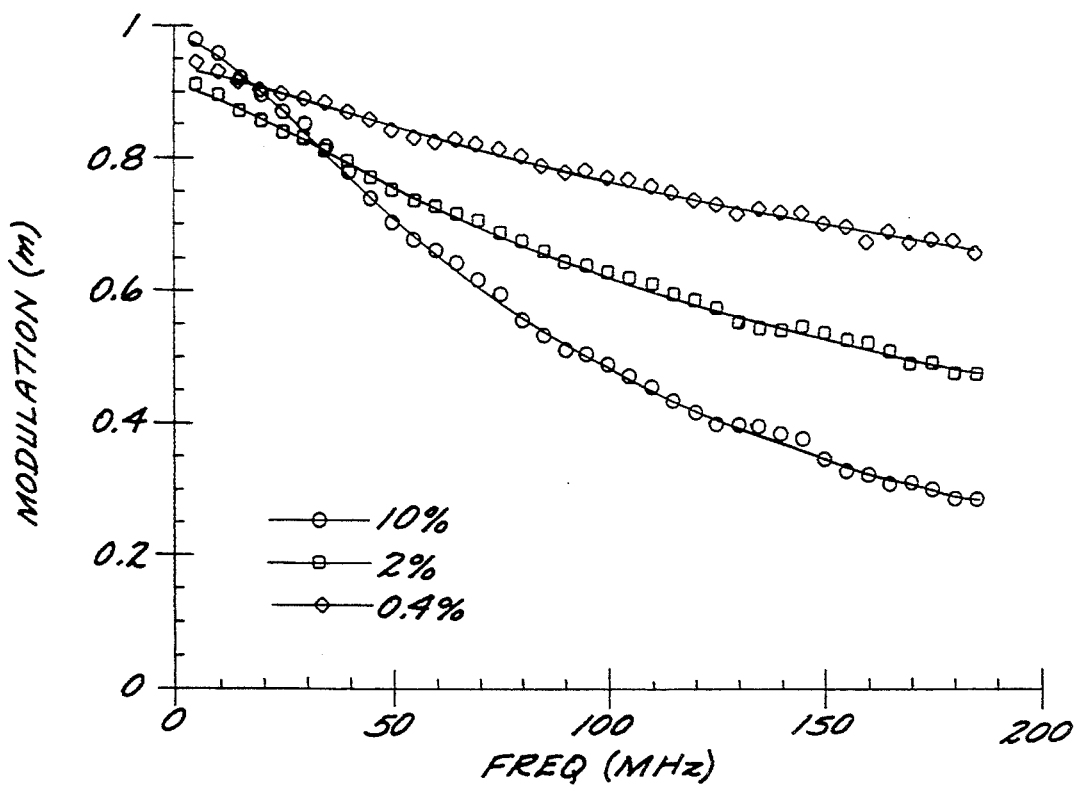
Figure 7A:
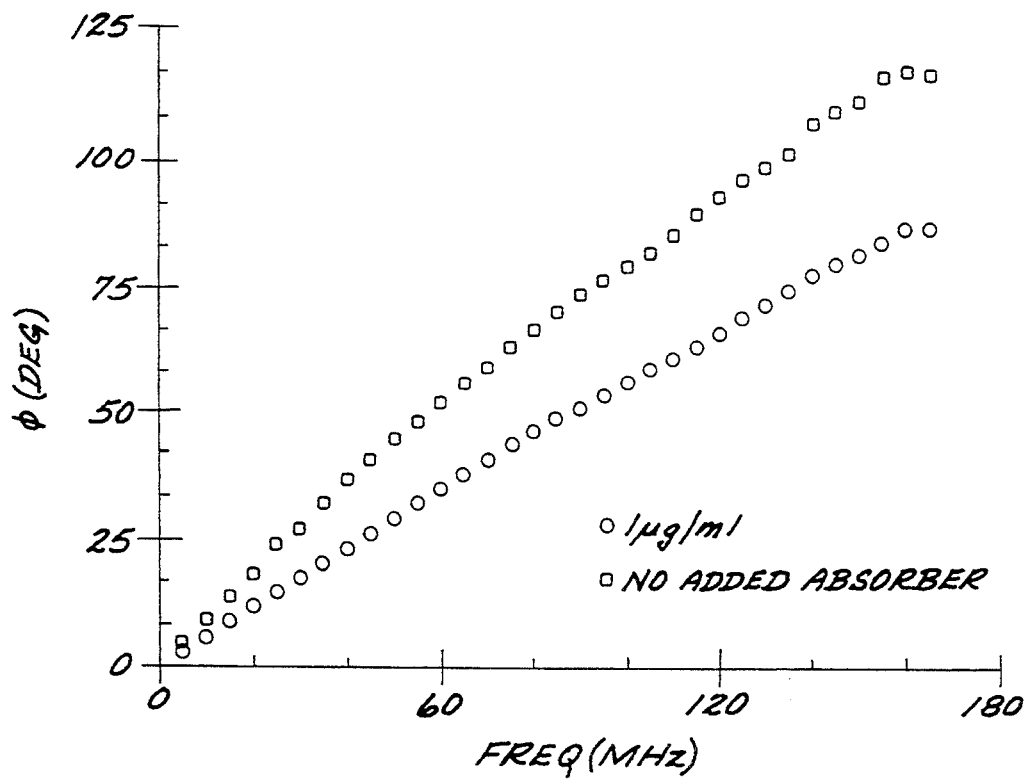
FIGS. 7a and 7b are graphs illustrating the effects of a TPPS$_4$ absorber on phase and modulation respectively in a 10 percent Intralipid solution.
Figure 7B:
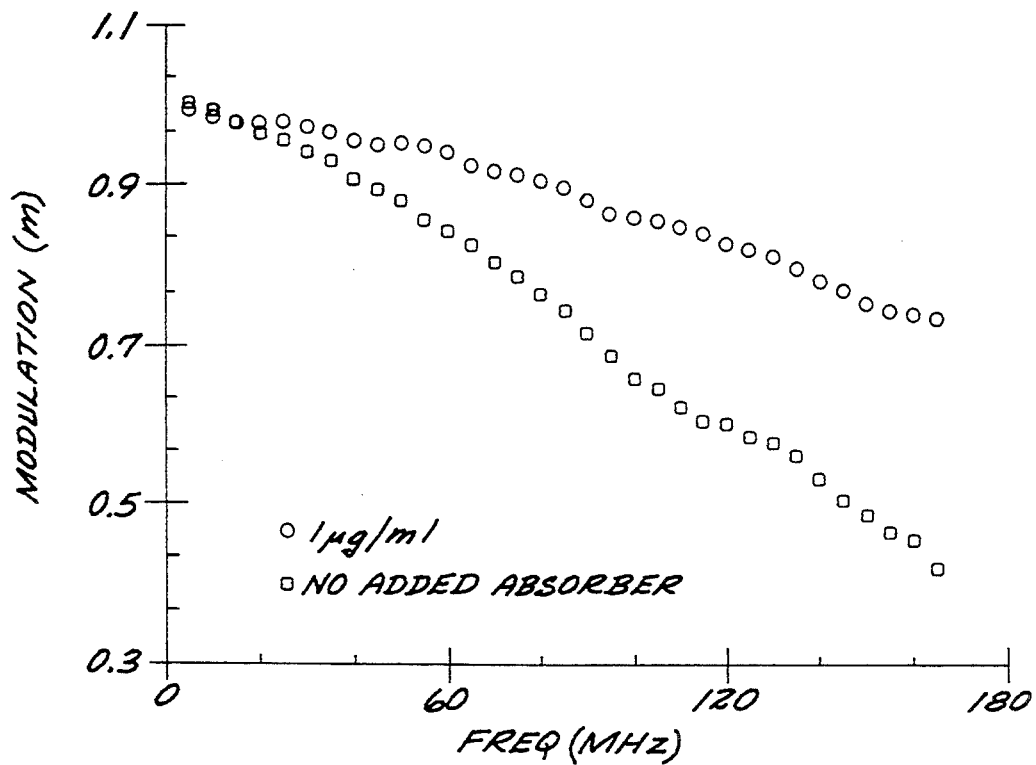

The exceptionally low phase velocities of the photon diffusion in the Intralipid solutions which are graphed in FIGS. 5a, 5b and 6 rarely occur in fact in in vivo tissue notwithstanding the scattering similarities between Intralipid and some tissues. In a more realistic comparison, as depicted in the graphical outputs of FIGS. 7a and 7b, the effects of a TPPS$_4$ absorber on phase and modulation respectively in a 10 percent Intralipid solution is illustrated. Modulation frequencies to 165 MHz are shown at a source-detector separation of 7.5 millimeters. There is a distinct nonlinearity to both phase and modulation as a function of frequency. Curves are shown with an Intralipid solution with no absorber added compared to one to which a one microgram per milliliter addition of TPPS$_4$ has been added. As more absorber is added, the frequency response flattens out. Phase decreases and attenuation increases with increasing absorber concentration. The additional absorber causes the photons to follow shorter paths to the detector. Thus there are fewer scattering events and a decrease in phase delay and modulation is observed. When the scattering coefficient is held constant, increasing the absorption coefficient results in higher phase velocities and longer modulation wavelengths.

Figure 8A:
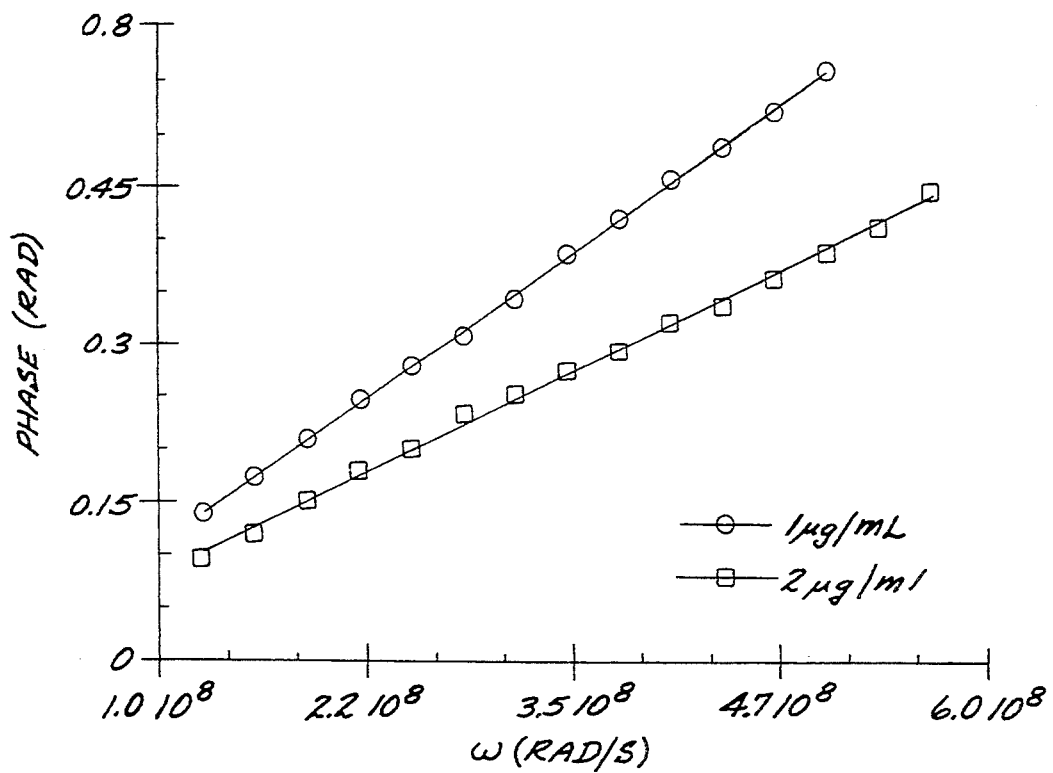
FIGS. 8a and 8b are graphs which redisplay some of the data in the depictions of FIGS. 7a and 7b as functions of $\omega$ and $\omega^2$ respectively.
Figure 8B:
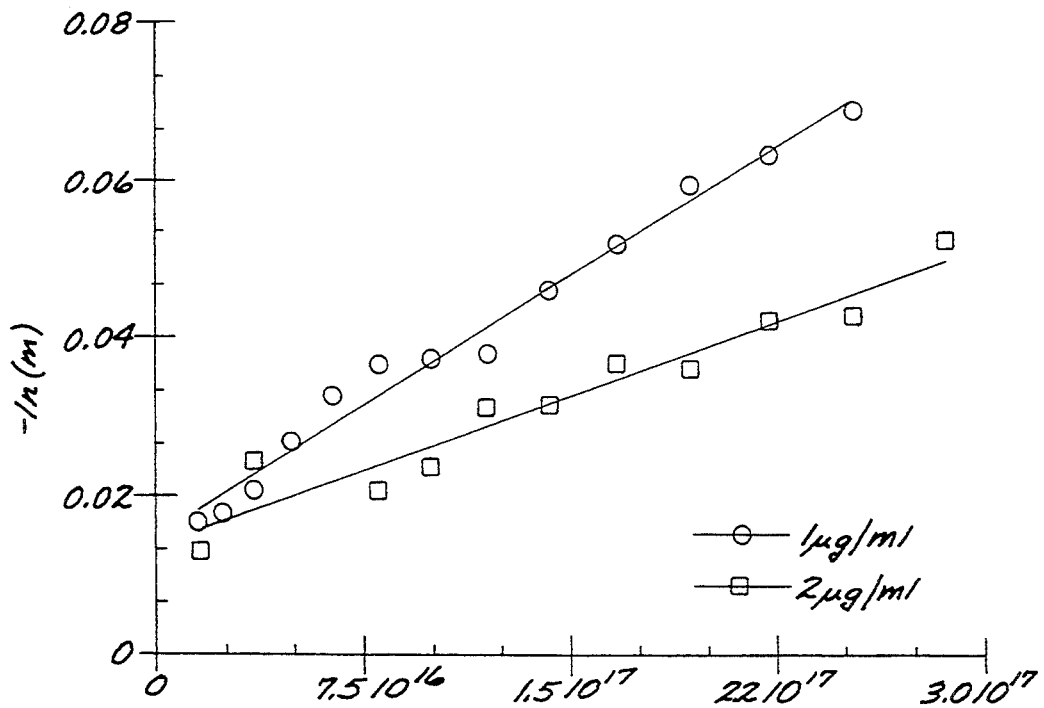

Under high absorption coefficients, such as when $\omega\tau$ is very much less than 1, the modulation may be close to or almost equal to unity since $k_r$ approaches $1/\delta$. If there is sufficient modulation to satisfy equation 19, the absorption coefficient can then be determined from equation 20. The graphical depictions of FIGS. 8a and 8b redisplay some of the data in the depictions of FIGS. 7a and 7b as functions of $\omega$ and $\omega^2$ respectively. FIGS. 8a and 8b illustrate the utility of a linear fit determination of the optical scattering and absorption coefficients in a highly absorptive material. Average $\beta$ values obtained from at least five separate distance measurements between the fibers is displayed in FIG. 9 as a function of concentration of TPPS$_4$.

Figure 9:
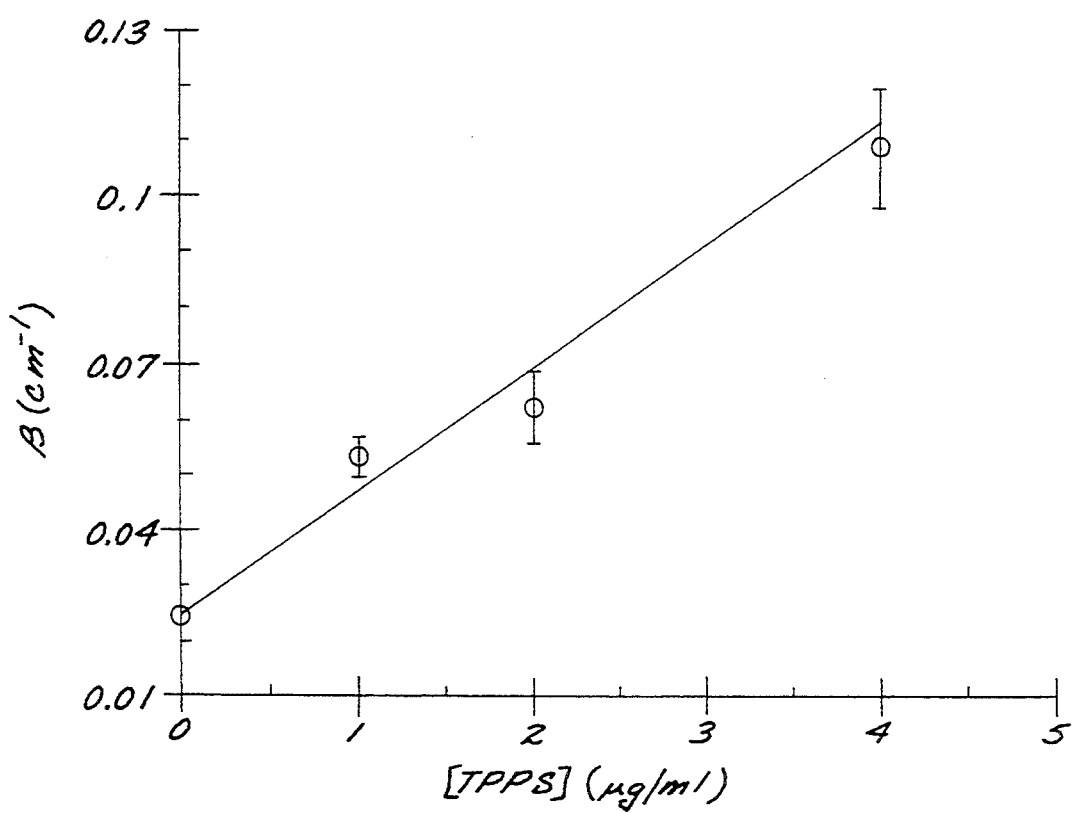
FIG. 9 is a graph which illustrates average $\beta$ values obtained from at least five separate distance measurements between the fibers as a function of concentration of TPPS$_4$.

The molar concentration of TPPS$_4$ in a 10 percent Intralipid solution as shown in FIG. 9, can be calculated from the relationship between the linear absorption coefficient $\beta$ and the molar extinction coefficient, $\epsilon$, that is $\beta = 2.3 \ \epsilon C$ where the $\epsilon$ for TPPS$_4$ is equal to $2.5 \times 10^4$ $M^{-1}cm^{-1}$ at 514 nanometers and C is the molar concentration. The linear appearance of the relationship shown in FIG. 9 indicates that relatively low absorption values can be reliably determined despite the presence of substantial scattering. In fact, scattering enhances detectability by slowing the phase velocity and reducing the modulation wavelength to dimensions that approach $1/\beta$. Assuming diffusion behavior, the accuracy of high beta determinations is generally limited by signal quality. Most measurements in tissue in the red or near infrared spectral regions, display some modulation using frequencies of up to 200 MHz. The somewhat poor modulation data depicted in FIG. 8b as compared to the phase data in FIG. 8a indicates that the slope of the modulation data obtained from the linear fit diminishes with increasing absorption coefficient, $\beta$. This decrease underscores the importance of acquiring multiple modulation frequencies.

Single frequency measurements can be employed to calculated the absorption coefficient $\beta$ by recognizing the linear relationship summarized in equation 19. Due primarily to variations in the precision of the modulation slope, however, the reliability of single frequency determinations may not be as high as multifrequency calculations. Obviously small variations in the modulation data can lead to large errors in the estimation of the absorption coefficient, $\beta$. Therefore, it is desirable to acquire the phase and modulation data for as many different frequencies as possible. In addition, by looking at the entire frequency response, it can be determined whether it is appropriate to apply the dispersion relationships in order to calculate the optical properties of scattering absorption coefficients.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

We claim:

1. An optical method of analysis of turbid media comprising the steps of:

generating a modulated optical radiance wave at more than two frequencies at 1 MHz and higher;

exposing a sample of said turbid media to said modulated radiance wave;

measuring said modulated radiance wave returned from said sample; and determining from said measured returned radiance wave an optical property of said sample, whereby said sample may be analyzed whether said sample is highly scattering, highly absorptive, or a combination of both.

2. The method of claim 1 wherein said step of generating said modulated radiance wave comprises the step of modulating said radiance wave at a plurality of frequencies.

3. The method claim 2 wherein said step of generating said plurality of frequencies comprises the step of modulating said radiance wave at a fundamental frequency and a plurality of integer harmonics thereof.

4. The method of claim 1 further comprising the step of generating said modulated radiance wave at a plurality of optical frequencies for the purpose of providing an absorption spectrum of said sample.

5. The method of claim 2 wherein step of measuring said radiance wave is performed at each of said plurality of frequencies and said step of determining comprises the step of providing a complete curve fit in the frequency domain in a computer automated process for at least one optical parameter derived from said radiance wave at said plurality of frequencies, said curve fit being determined by the coefficient of absorption and the coefficient of scattering for said sample so that said sample can be quantitatively analyzed by identification of its optical absorption and scattering coefficients.

6. The method of claim 5 further comprising the step wherein said complete curve fit is also determined by concentration of an absorbing and/or scattering substance within said sample so that the quantitative concentration of said substance is determined.

7. The method of claim 2 wherein said sample is highly absorptive and where said step of determining comprises the step of providing a linear curve fit in the frequency domain to at least one optical parameter derived from said measured radiance wave at and below a predetermined frequency, said linear curve fit being determine by the absorption coefficient of said sample so that quantitative determination of said sample may be made.

8. The method of claim 7 further comprising the step of determining said linear curve fit below said predetermined frequency according to concentration of a substance included within said sample so that quantitative determination of said substance may be made.

9. The method of claim 1 wherein said step of measuring said radiance wave comprises the derivation of modulation of said light, said modulation being defined as modulation of light returned from said sample relative to modulation of said light exposed on said sample.

10. The method of claim 1 wherein said step of measuring said radiance wave comprises the derivation of the phase lag of said light, said phase lag being defined as the phase of light returned from said sample relative to the phase of said light exposed on said sample.

11. The method of claim 1 wherein said step of measuring said radiance wave comprises the steps of receiving said returned radiance wave from said sample in a sensing device having a gain, said gain of said sensing device being modulated at a fundamental frequency increased by a cross correlation frequency and integer multiharmonics thereof.

12. The method of claim 11 wherein said step of determining comprises the step of analyzing phase and modulation amplitude response at each of said harmonic cross frequencies returned from said sample.

13. The method claim 12 wherein said step of analyzing comprises transforming phase and modulation response return from said sample to a frequency spectrum.

14. An apparatus for analyzing turbid media comprising:
means for exposing a sample to a modulated radiance wave at more than two frequencies in the range of 1 MHz or higher;
means for receiving at least a portion of said modulated radiance wave returned from said sample;
means for analyzing said returned modulated radiance wave from said sample at least one cross frequency of the frequency of modulation of said radiance wave;
means for providing a frequency spectrum of said analyzed radiance wave at said at least one cross frequency; and
means for providing a curve fit to said frequency spectrum according to the optical absorption coefficient, and optical scattering coefficient as curve fitting parameters,
whereby optical properties of said sample are identified whether said sample is high absorptive, highly scattering or both.

15. The apparatus of claim 14 wherein said means for exposing said sample to said modulated beam of light modulates said radiance wave at a predetermined fundamental frequency and integer harmonics thereof.

16. The apparatus of claim 15 wherein said means for analyzing said returned radiance wave from said sample at least one cross frequency preferentially detects said return radiance wave at a plurality of integer harmonics above said fundamental frequency.

17. The apparatus of claim 16 wherein said means for providing a curve fit to said frequency spectrum provides a complete nonlinear curve fit at said plurality of cross frequency harmonics so that a highly scattering sample may be analyzed.

18. The apparatus of claim 16 wherein said means for providing a curve fit provides a linear curve fit to said frequency spectrum at and below a predetermined frequency so that a highly absorptive sample may be analyzed.

19. The apparatus of claim 14 wherein said fundamental frequency is 5 Mhz and wherein said cross frequency is 3 Hz above said fundamental frequency and at integer harmonics thereof.

20. The apparatus of claim 14 wherein said means for providing a frequency spectrum provides a frequency spectrum of phase lag and/or modulation of said radiance wave returned from said sample.

* * * * *